United States Patent [19]

Born et al.

[11] Patent Number: 4,609,940
[45] Date of Patent: Sep. 2, 1986

[54] RADIODIAGNOSTIC INSTALLATION WITH A PATIENT TABLE AND A PRIMARY RADIATION DIAPHRAGM

[75] Inventors: Hans-Joachim Born, Moehrendorf; Hartmut Duschka, Uttenreuth; Gerhard Seyler, Bubenreuth; Wolfgang Zerl, Herzogenaurach, all of Fed. Rep. of Germany

[73] Assignee: Siemens Aktiengesellschaft, Berlin and Munich, Fed. Rep. of Germany

[21] Appl. No.: 641,796

[22] Filed: Aug. 17, 1984

[30] Foreign Application Priority Data

Aug. 24, 1983 [DE] Fed. Rep. of Germany ....... 3330552

[51] Int. Cl.⁴ .................. H04N 5/32; H04N 5/30; A61B 6/08
[52] U.S. Cl. .................................. 358/111; 358/110; 378/99; 378/205; 378/209
[58] Field of Search ............... 378/99, 20, 208, 209, 378/205, 131; 358/111, 110; 250/491.1

[56] References Cited

U.S. PATENT DOCUMENTS 3,991,317 11/1976 Kunne et al. ............... 250/445 R
4,174,481 11/1979 Liebetruth ...................... 378/99
4,245,244 1/1981 Lijewski et al. ................ 358/111

FOREIGN PATENT DOCUMENTS 2655661 6/1978 Fed. Rep. of Germany ......... 378/4
3030332 2/1982 Fed. Rep. of Germany ...... 378/151

Primary Examiner—Craig E. Church
Assistant Examiner—Charles Wieland
Attorney, Agent, or Firm—Mark H. Jay

[57] ABSTRACT

The invention relates to a radiodiagnostic installation with a motor-adjustable patient table, a motor-adjustable radiation diaphragm, and an image intensifier television system for image reproduction. With the monitor of the image intensifier television system a light pen is associated for the entry of certain sites on the monitor into a memory. Connected to the memory are control circuits for the motors of the patient table and of the primary radiation diaphragm, which are designed so that the patient table and the primary radiation diaphragm are adjusted in accordance with the respective image field on the monitor to which the light pen points.

3 Claims, 3 Drawing Figures

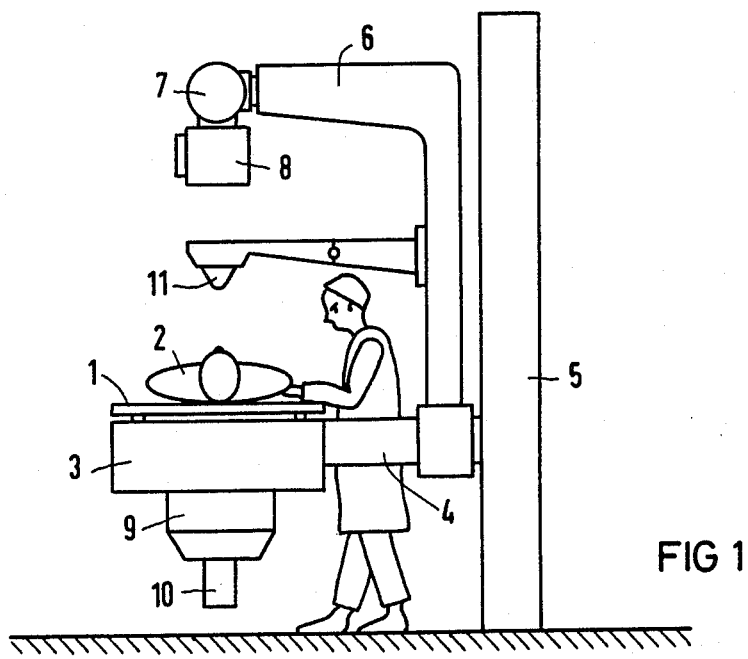
FIG 1
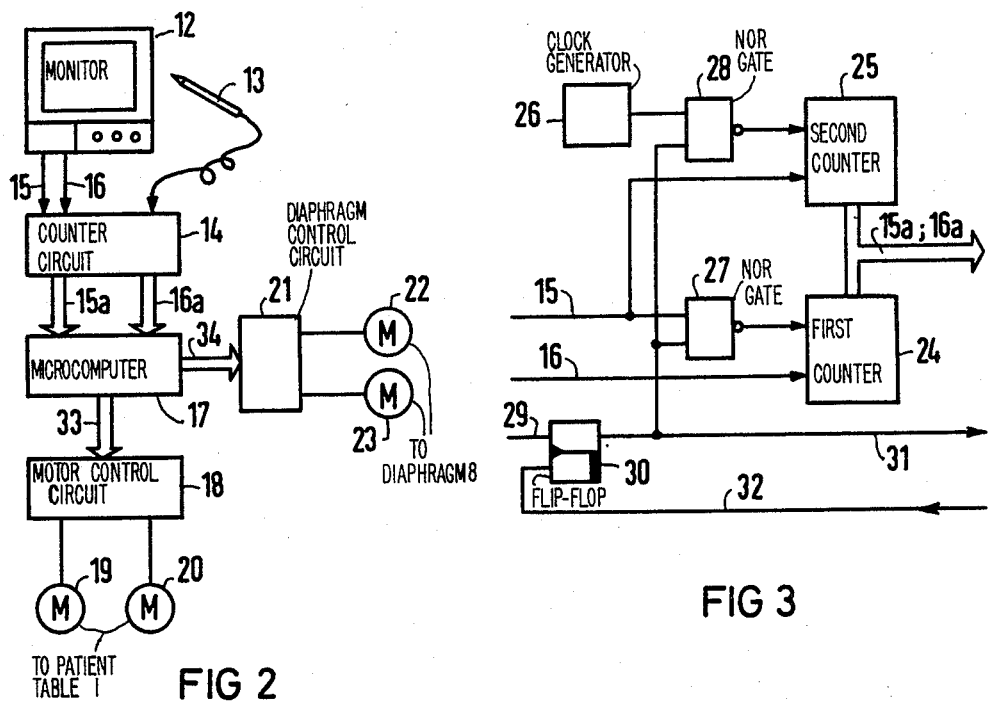
FIG 2
FIG 3

RADIODIAGNOSTIC INSTALLATION WITH A PATIENT TABLE AND A PRIMARY RADIATION DIAPHRAGM

BACKGROUND OF THE INVENTION

The invention relates to a radiodiagnostic installation with a motor-adjustable table, a motor-adjustable primary radiation diaphragm, and an image intensifier television system for image reproduction.

Radiodiagnostic installations of this kind produce an x-ray picture of a patient on a television monitor. To select the particular radiated region for a roentgenogram, the patient table is moved under fluoroscopy into a desired position, in which the desired part of the patient is displayed. Also, the primary radiation diaphragm is adjusted in accordance with the dimensions of this part. Therefore, complicated and time-consuming adjustment and selection procedures are required before an x-ray picture is taken. In particular it is often necessary to repeatedly alternate operating procedures, i.e. first to adjust the table by respective motor control, then to actuate the diaphragm, then to correct the position of the table, and so forth.

It is the object of the invention to provide a radiodiagnostic installation of the initially mentioned kind which minimizes the adjusting procedures required before an exposure, in particular before an indirect exposure.

According to the invention, there is assigned to the monitor a light pen for the entry of certain sites on the monitor into a memory. A control circuit is connected to the memory for controlling the motors of the patient table, the control circuit being designed so that the table is centered relative to the particular site on the monitor to which the light pen points. To adjust the patient table for the next exposure, it suffices to mark the center of the next region desired with the light pen on the monitor, while the current patient region is displayed. Thereafter the patient table is automatically motor-adjusted so that the marked region lies in the center of the picture.

In a preferred embodiment of the invention a diaphragm control circuit is provided for control of the primary radiation diaphragm in accordance with the particular picture field selected by the light pen. With this feature, not only is the patient table moved into the correct position by the marking of the region of interest on the viewer, but the primary radiation diaphragm is also automatically motor-adjusted in such a way that the desired region is focused.

BRIEF DESCRIPTION OF THE DRAWINGS

The invention will now be explained more specifically with reference to a preferred embodiment illustrated in the following exemplary and non-limiting drawings, in which:

FIG. 1 schematically shows a radiodiagnostic installation which includes the invention;

FIG. 2 schematically shows a block diagram if a part of the radiodiagnostic installation according to FIG. 1; and FIG. 3 is a schematic diagram of a part of FIG. 2.

DETAILED DESCRIPTION OF PREFERRED EMBODIMENTS

In FIG. 1 a patient table 1 is illustrated, on which rests a patient 2, of whom roentgenograms are to be made. Table 1 is shiftable by motor on a frame 3. Frame 3 is secured on a support 4, which is mounted on a stand 5 to be vertically adjustable. Support 4 carries an arm 6 with an x-ray tube 7 which emits the radiation passing through the patient 2. This radiation is focused on the desired region by a motor-adjustable primary radiation diaphragm 8. The x-ray picture is picked up by an image intensifier 9, which is followed by a television camera 10. A compression cone 11 serves to compress the patient 2 and is mounted for this purpose on arm 6, which is vertically adjustable.

The picture taken by the television camera 10 is reproduced on a monitor 12 (FIG. 2), to which a light pen 13 is assigned for marking the region of interest. For adjusting the patient table 1 and the primary radiation diaphragm 8 with the aid of electric motors, the region of interest is marked with the light pen 13 and thereafter the patient table 1 and primary radiation diaphragm 8 are automatically adjusted so that the marked region appears in the center of the monitor 12 and is optimally focused, so that overradiation of the reproduced picture is avoided. To this end the light pen 13 is connected to a counter circuit 14, to which the horizontal pulses are supplied from the monitor 12 via a line 15 and the vertical pulses via a line 16. When the light pen 13 is placed on a particular site of the picture on the monitor 12, the coordinates of this site can be polled from the counter circuit 14, where they are temporarily stored in a manner to be described below in connection with FIG. 3. The x-coordinate on monitor 12 is transmitted through the data line 15a and y-coordinate through the data line 16a, to a microcomputer 17 which via a motor control circuit 18 actuates the two motors 19 and 20 for longitudinal and transverse displacement of the patient table 1 in such a way that the latter moves the marked area into the center of the picture on the monitor 12.

Via a diaphragm control circuit 21 the microcomputer 17 further causes actuation of the motors 22 and 23 for adjustment of the primary radiation diaphragm 8, namely of the diaphragm plate pair for focusing in x-direction and of the diaphragm plate pair for focusing in y-direction accordingly.

The result is that by marking the relevant region on the monitor 12 with aid of the light pen 13, optimum adjustment both of the patient table 1 and of the primary radiation diaphragm 8 automactically occurs. No other adjusting manipulation are necessary.

FIG. 3 shows the construction of the counter circuit 14 for determining that site on monitor 12 to which the light pen 13 points. The counter circuit 14 comprises a first counter 24 for the horizontal pulses on line 15 and a second counter 25 for the clock pulses of a clock generator 26. The clock frequency of the clock generator 26 is selected so that its pulses divide each image line in accordance with a desired line resolution. The first counter 24 is resettable by each vertical pulse on line 16, and the second counter 25 by each horizontal pulse on line 15. The counters 24 and 25 are driven via NOR gates 27 and 28. The respective counter status can be preserved by a pulse on line 29 which drives the counters 24 and 25 via a flip-flop 30 and is supplied by the light pen 13.

If the light pen 13 does not point to the monitor 12, the counters 24 and 25 are advanced in accordance with the movement of the electron beam of monitor 12, i.e. the status of counter 24 corresponds to the respective scanned image line, since this counter 24 counts the horizontal pulses and is reset to zero by each vertical pulse. The status of counter 25 corresponds to the point reached by the electron beam in the respective line, since this counter 25 is set to zero by each horizontal pulse and counts the pulses of the clock generator 26 for each image line.

When the light pen 13 is placed on a particular site of monitor 12, a pulse is generated on line 29 which via the flip-flop 30 preserves the counts of the counters 24 and 25. At the same time an interrupt pulse is sent via line 31 to the microcomputer 17, which thereupon polls the counts via the data lines 15a and 16a. After such polling the microcomputer 17 delivers an enable pulse via the control line 32, so that the counters 24 and 25 start to count again and are ready for pickup of the next site on monitor 12 to which the light pen 13 is pointed. The microcomputer 17 then in turn causes via lines 33 and 34 (FIG. 2) the adjustment of the patient table 1 and of the primary radiation diaphragm 8.

Those skilled in the art will understand that changes can be made in the preferred embodiments here described, and that these embodiments can be used for other purposes. Such changes and uses are within the scope of the invention, which is limited only by the claims which follow.

What is claimed is:

1. Radiodiagnostic apparatus comprising:
   a motor-operated primary radiation diaphragm;
   a patient table;
   motor means for moving the patient table along two different directions in a plane;
   means for reproducing an image of that region of a patient on the patient table which is to be irradiated through the radiation diaphragm, said reproducing means including a monitor;
   a light pen for selecting sites on the monitor;
   memory means for registering a location of a selected site on the monitor; and
   control means for operating the motor means in a manner that that point on the patient which corresponds to said site is brought to the center of said region.

2. The apparatus of claim 1, wherein said memory means comprises
   a first counter for counting horizontal pulses from the monitor; and
   a second counter for counting clock pulses from a clock generator with a frequency chosen to divide an image line of the monitor with a desired resolution, the first counter being resettable by each vertical pulse from the monitor and the second counter being resettable by each horizontal pulse from the monitor, and the counters being connected to the light pen in a manner that the states of the counters are preserved when the election beam of the monitor reaches said site
   and where the apparatus further comprises
   a microcomputer connected to the counters and reading the counts registered by the counters, and
   motor control means for controlling the motor means.

3. The apparatus of claims 1, further comprising means for operating the diaphragm and properly focusing it to emcompass said region.

* * * * *